US012600361B2

(12) United States Patent
Glaser et al.

(10) Patent No.: US 12,600,361 B2
(45) Date of Patent: Apr. 14, 2026

(54) VEHICLE DRIVER IMPAIRMENT DETECTOR SYSTEM AND METHOD

(71) Applicant: GM Global Technology Operations LLC, Detroit, MI (US)

(72) Inventors: Daniel S. Glaser, Novi, MI (US); Joseph F. Szczerba, Grand Blanc, MI (US); Sri Krishna Divya Pemmaraju, Plymouth, MI (US); Yi Guo Glaser, Novi, MI (US); Ron Hecht, Raanana (IL); Omer Tsimhoni, Warren, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 168 days.

(21) Appl. No.: 18/485,527

(22) Filed: Oct. 12, 2023

(65) Prior Publication Data

US 2025/0121830 A1 Apr. 17, 2025

(51) Int. Cl.
*B60W 40/08* (2012.01)
*A61B 5/00* (2006.01)

(52) U.S. Cl.
CPC .......... *B60W 40/08* (2013.01); *A61B 5/4863* (2013.01); *B60W 2040/0836* (2013.01); *B60W 2540/24* (2013.01)

(58) Field of Classification Search
CPC ......... B60W 40/08; B60W 2040/0836; B60W 2540/24; B60W 2050/146; A61B 5/4863; A61B 5/18; A61B 5/163; A61B 5/4845; B60K 28/063
USPC ........................................................ 701/113
See application file for complete search history.

(56) References Cited

U.S. PATENT DOCUMENTS

| | | | |
|---|---|---|---|
| 2018/0339706 A1* | 11/2018 | Biondo | B60W 50/10 |
| 2024/0293080 A1* | 9/2024 | Chung | A61B 5/18 |
| 2025/0121843 A1* | 4/2025 | Avadhanam | B60W 50/12 |

FOREIGN PATENT DOCUMENTS

| | | |
|---|---|---|
| DE | 102011119261 A1 | 5/2013 |
| DE | 102018112076 A1 | 11/2018 |

OTHER PUBLICATIONS

Abadi. et al., Analysing nystagmus waveforms: a computational framework, Scientific Reports 11, 9761 (2021). https://doi.org/10.1038/s41598-021-89094-7.
Juhola et al., The Classification of Valid and Invalid Beats of Three-Dimensional Nystagmus Eye Movement Signals Using Machine Learning Methods, Advances in Artificial Neural Systems. Jan. 2013, pp. 1-11, DOI:10.1155/2013/972412.

(Continued)

*Primary Examiner* — Scott A Reinbold
(74) *Attorney, Agent, or Firm* — Vivacqua Crane, PLLC

(57) ABSTRACT

A system for detecting an impairment of an operator of a vehicle includes an alcohol sensor, a camera, a start control, and a controller in electrical communication with the alcohol sensor, the camera, and the start control, the controller including a processor and a memory, the memory including instructions such that the processor is programmed to: determine that alcohol is detected using the alcohol sensor, disable the start control based on the detection of alcohol, perform a gaze nystagmus assessment of the operator using the camera, determine if the operator is impaired based on the gaze nystagmus assessment, and enable the start control when the operator is not impaired.

11 Claims, 6 Drawing Sheets

(56) References Cited

OTHER PUBLICATIONS

Papageorgiou, et al., Nystagmus in Childhood, Pediatrics & Neo-natology, 2014, pp. 1-11, DOI:10.1016/j.pedneo.2014.02.007.

Pasquariello et al., Characterisation of baseline oscillation in con-genital nystagmus eye movement recordings, Biomedical Signal Processing and Control, 2009, pp. 102-107, vol. 4, Issue 2, ISSN 1746-8094, https://doi.org/10.1016/j.bspc.2009.01.003. (https://www.sciencedirect.com/science/article/pii/S1746809409000044).

* cited by examiner

1

VEHICLE DRIVER IMPAIRMENT DETECTOR SYSTEM AND METHOD

INTRODUCTION

The present disclosure relates to a vehicle operator impairment detector system and method, and more particularly to a vehicle operator impairment detector system and method that detects whether a vehicle operator is expressing physical signs of alcohol impairment.

Operator impairment while operating a vehicle increases the risks of crashes. In an attempt to reduce this risk, detection solutions are proposed. One such solution is to use an in-vehicle chemical alcohol detector, such as the Operator Alcohol Detection System for Safety. The in-vehicle alcohol detector uses chemical sensors and algorithms that estimate BAC from the operator's breath. In addition, BAC may also be estimated by shining an infrared light through the fingertip of the operator and leveraging absorption algorithms. While these alcohol detector systems can provide accurate BAC measurements, there is a need in the art for a operator impairment detector that uses existing systems within the vehicle and is reliable and consistent. Particularly in cases where these former technologies are not present and/or yielded erroneous measures.

SUMMARY

A system for detecting an impairment of an operator of a vehicle is provided. The system includes an alcohol sensor, a camera, a start control, and a controller in electrical communication with the alcohol sensor, the camera, and the start control, the controller including a processor and a memory, the memory including instructions such that the processor is programmed to: determine that alcohol is detected using the alcohol sensor, disable the start control based on the detection of alcohol, perform a gaze nystagmus assessment of the operator using the camera, determine if the operator is impaired based on the gaze nystagmus assessment, and enable the start control when the operator is not impaired.

In one aspect, the processor is further programmed to perform the gaze nystagmus assessment of the operator using at least one of a display assessment using a display in the vehicle, an auditory assessment using an audio system in the vehicle, and a passive assessment.

In another aspect, the processor is further programmed to perform the gaze nystagmus assessment of the operator by tracking an eye movement of the operator and recording gaze samples over time during the eye movement, wherein the gaze samples include horizontal positions of the eyes during the eye movement of the operator at time intervals.

In another aspect, the processor is further programmed to determine if the operator is impaired by passing the gaze samples through a gaze nystagmus model.

In another aspect, the processor is further programmed to transform the gaze samples by deriving the horizontal positions of the eyes twice to determine a velocity and an acceleration at each time interval, wherein the velocity and acceleration are approximated or smoothed, and estimate a Gaussian Mixture Model using the derivatives of the horizontal positions of the eyes to determine if there are micro eye movements during the time intervals and to determine an amplitude and frequency of the micro eye movements at the time intervals.

In another aspect, the processor is further programmed to determine if the operator is impaired by determining if there are micro eye movements during the time intervals during the eye movement, determine if there are micro eye movements during the time intervals at a maximum horizontal eye position, and determine if there are micro eye movements during the time intervals prior to forty-five degrees from a center during eye movement.

In another aspect, wherein the processor is further programmed to determine if the operator is impaired by comparing the amplitude and the frequency of the micro eye movements during the eye movement to a first amplitude threshold and a first frequency threshold, and determine nystagmus is detected when the amplitude and the frequency during the eye movement is greater than the first amplitude threshold and the first frequency threshold.

In another aspect, the processor is further programmed to determine if the operator is impaired by comparing the amplitude and the frequency of the micro eye movements during the time intervals at the maximum horizontal eye position to a second amplitude threshold and a second frequency threshold, and determine nystagmus is detected when the amplitude and the frequency during the time intervals at the maximum horizontal eye position is greater than the second amplitude threshold and the second frequency threshold.

In another aspect, the processor is further programmed to determine if the operator is impaired by comparing the amplitude and the frequency of the micro eye movements during the time intervals prior to forty-five degrees from the center during eye movement to a third amplitude threshold and a third frequency threshold, and determine nystagmus is detected when the amplitude and the frequency during the time intervals prior to forty-five degrees from the center during eye movement is greater than the third amplitude threshold and the third frequency threshold.

In another aspect, the processor is further programmed to assign a score for each eye based on whether nystagmus was detected during the time intervals and comparing the score to an impairment threshold, and determine the operator is impaired when the score exceeds the impairment threshold.

In another embodiment, a method for detecting an impairment of a operator of a vehicle is provided. The method includes determining that alcohol is detected using an alcohol sensor disposed within the vehicle, disabling a start control based on the detection of alcohol within the vehicle, performing a gaze nystagmus assessment of the operator using a camera within the vehicle, determining that the operator is not impaired based on the gaze nystagmus, and enabling the start control when the operator is not impaired.

In one aspect, performing the gaze nystagmus assessment of the operator includes using at least one of a display assessment using a display in the vehicle, an auditory assessment using an audio system in the vehicle, and a passive assessment.

In another aspect, performing the gaze nystagmus assessment of the operator includes tracking an eye movement of the operator and recording gaze samples over time during the eye movement, wherein the gaze samples include horizontal positions of the eyes during the eye movement of the operator at time intervals.

In another aspect, determining if the operator is impaired includes transforming the gaze samples by deriving the horizontal positions of the eyes twice to determine a velocity and an acceleration at each time interval, wherein the velocity and acceleration are approximated or smoothed, and estimating a Gaussian Mixture Model using the derivatives of the horizontal positions of the eyes to determine if there are micro eye movements during the time intervals and to determine an amplitude and frequency of the micro eye movements at the time intervals.

In another aspect, determining if the operator is impaired includes determining if there are micro eye movements during the time intervals during the eye movement, determining if there are micro eye movements during the time intervals at a maximum horizontal eye position, and determining if there are micro eye movements during the time intervals prior to forty-five degrees from a center during eye movement.

In another aspect, determining if the operator is impaired includes comparing the amplitude and the frequency of the micro eye movements during the eye movement to a first amplitude threshold and a first frequency threshold, and determining nystagmus is detected when the amplitude and the frequency during the eye movement is greater than the first amplitude threshold and the first frequency threshold.

In another aspect, determining if the operator is impaired includes comparing the amplitude and the frequency of the micro eye movements during the time intervals at the maximum horizontal eye position to a second amplitude threshold and a second frequency threshold, and determining nystagmus is detected when the amplitude and the frequency during the time intervals at the maximum horizontal eye position is greater than the second amplitude threshold and the second frequency threshold.

In another aspect, determining if the operator is impaired includes comparing the amplitude and the frequency of the micro eye movements during the time intervals prior to forty-five degrees from the center during eye movement to a third amplitude threshold and a third frequency threshold, and determining nystagmus is detected when the amplitude and the frequency during the time intervals prior to forty-five degrees from the center during eye movement is greater than the third amplitude threshold and the third frequency threshold.

In another aspect, the method further includes assigning a score for each eye based on whether nystagmus was detected during the time intervals and comparing the score to an impairment threshold, and determining the operator is impaired when the score exceeds the impairment threshold.

In yet another embodiment, a system for detecting an impairment of an operator of a vehicle is provided. The system includes an alcohol sensor, a camera, a display on the vehicle, a start control, a controller in electrical communication with the alcohol sensor, the camera, the display, and the start control, the controller including a processor and a memory, the memory including instructions such that the processor is programmed to: determine that alcohol is detected using the alcohol sensor, disable the start control based on the detection of alcohol, perform a gaze nystagmus assessment of the operator including displaying a graphic on the display, instructing the operator to follow the graphic on the display with their eyes, and tracking an eye movement using the camera to record gaze samples over time intervals, transform the gaze samples by deriving horizontal positions of the eyes twice to determine a velocity and an acceleration at each time interval, wherein the velocity and acceleration are approximated or smoothed, estimate a Gaussian Mixture Model using the derivatives of the horizontal positions of the eyes to determine if there are micro eye movements during the time intervals, determine an amplitude and frequency of the micro eye movements at the time intervals when there are micro eye movements, compare the amplitude and frequency of the micro eye movements throughout a full eye movement, at a maximum eye position, and prior to a midpoint of the full eye movement to one or more thresholds, assign a score for each eye when the amplitude and frequency of the micro eye movements at the full eye movement, at the maximum eye position, and prior to the midpoint of the full eye movement exceeds the one or more thresholds, compare the score to an impairment score, and enable the start control when the score is less than the impairment score and disable the start control when the score is greater than or equal to the impairment score.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
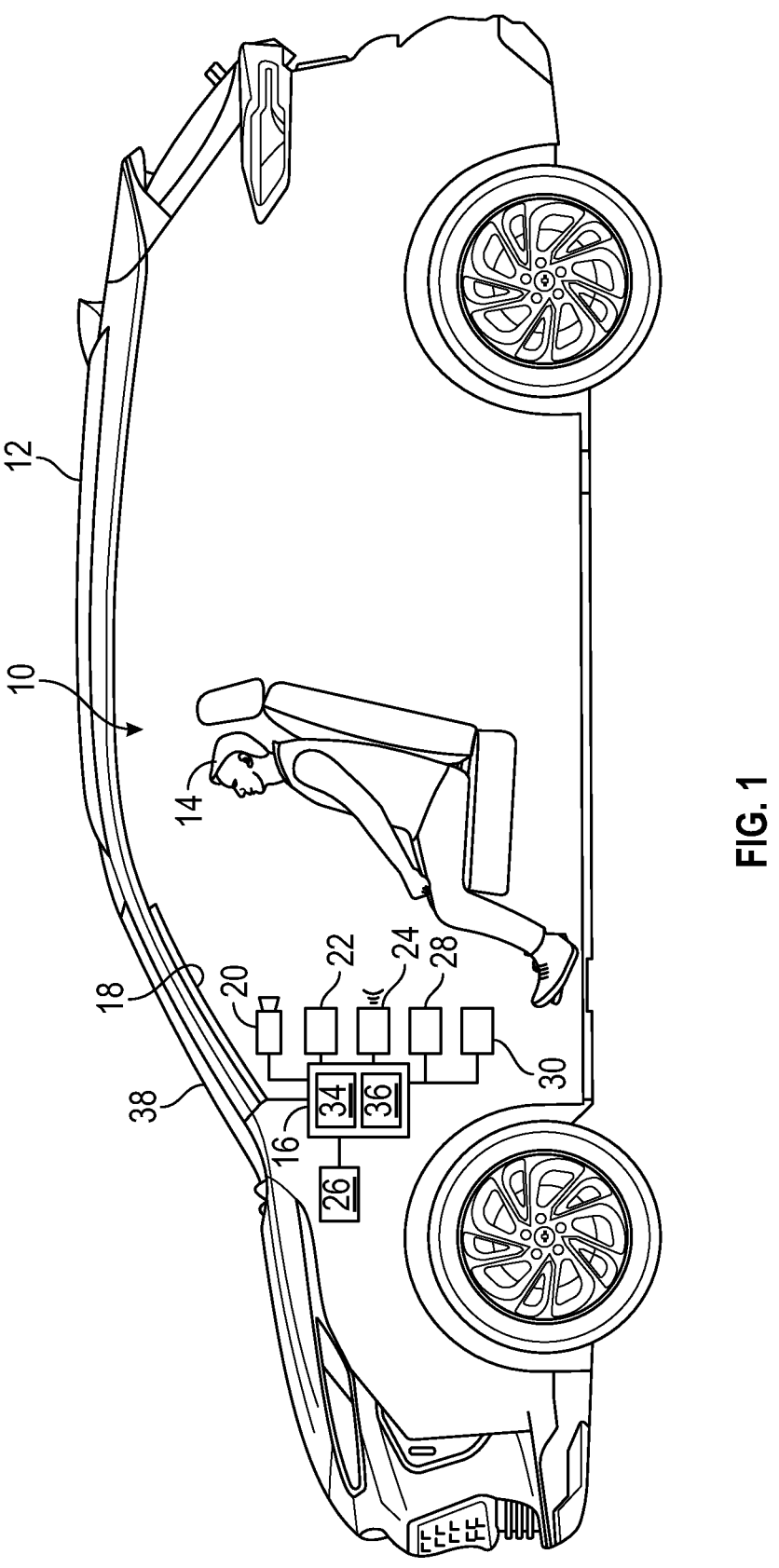
FIG. 1 is a schematic diagram of a vehicle operator impairment detector system in a vehicle according to an exemplary embodiment.

Referring to FIG. 1, a vehicle operator impairment detector system is illustrated and generally indicated by reference number 10. The vehicle operator impairment detector system 10 is shown with an exemplary vehicle 12. While a passenger vehicle is illustrated, it should be appreciated that the vehicle 12 may be any type of vehicle or equipment without departing from the scope of the present disclosure. The vehicle operator impairment detector system 10 is used to detect gaze nystagmus of a operator 14 of the vehicle 12 in order to determine operator impairment, as will be described in greater detail below. The vehicle operator impairment detector system 10 generally includes a controller 16, a display 18, a camera 20, an alcohol sensor 22, an audio system 24, a operator monitoring system 26, a human machine interface (HMI) 28, and a start control 30.

The controller 16 is used to implement a method 100 for detecting impairment of the operator 14 of the vehicle 12, as will be described below. The controller 16 includes at least one processor 34 and a non-transitory computer readable storage device or media 36. The processor 34 may be a custom made or commercially available processor, a central processing unit (CPU), a graphics processing unit (GPU), an auxiliary processor among several processors associated with the controller 16, a semiconductor-based microprocessor (in the form of a microchip or chip set), a macroprocessor, a combination thereof, or generally a device for executing instructions. The computer readable storage device or media 36 may include volatile and nonvolatile storage in read-only memory (ROM), random-access memory (RAM), and keep-alive memory (KAM), for example. KAM is a persistent or non-volatile memory that may be used to store various operating variables while the processor 34 is powered down. The computer-readable storage device or media 36 may be implemented using a number of memory devices such as PROMs (programmable read-only memory), EPROMs (electrically PROM), EEPROMs (electrically erasable PROM), flash memory, or another electric, magnetic, optical, or combination memory devices capable of storing data, some of which represent executable instructions, used by the controller 16 to control various systems of the vehicle 12. The controller 16 may also consist of multiple controllers which are in electrical communication with each other. The controller 16 may be inter-connected with additional systems and/or controllers of the vehicle 12, allowing the controller 16 to access data such as, for example, speed, acceleration, braking, and steering angle of the vehicle 12.

The controller 16 is in electrical communication with the display 18, the camera 20, the alcohol sensor 22, the audio system 24, the operator monitoring system 26, the human machine interface (HMI) 28, and the start control 30.

In an exemplary embodiment, the electrical communication is established using, for example, a CAN bus, a Wi-Fi network, a cellular data network, or the like. It should be understood that various additional wired and wireless techniques and communication protocols for communicating with the controller 16 are within the scope of the present disclosure.

The display 18 is used to perform a guided assessment during the method for detecting impairment of the operator 14. The display 18 is a wide view display such as, for example, a wide-view display on a console of the vehicle 12, a full windshield head up display (HUD) on a windshield 38 of the vehicle 12, a wide-view reflective or diffractive HUD including a pillar-to-pillar display on the windshield 38 of the vehicle 12, or any other type of wide-view display.

The camera 20 is used to capture images of the eyes, and in particular the pupils, of the operator 14. The camera 20 is therefore mounted within the vehicle 12 forward of the operator 14. The camera 20 may be any type of in-vehicle camera and may include various lens types including, for example, wide-angle lenses and/or narrow-angle lenses, and/or infrared light emitting diode (LED) lighting to induce corneal reflection, thus improving detection of the eyes.

The alcohol sensor 22 forms part of a Operator Alcohol Detection System for Safety (DADDS) system. The alcohol sensor 22 is used to determine a blood-alcohol level of the operator 14. The alcohol sensor 22 may be a chemical sensor that measures alcohol from the operator's breathing. Alternatively, the alcohol sensor 22 may be an infra-red emitter and detector that measures blood alcohol by shining an infrared light through the fingertip of the operator 14. Various other types of alcohol sensors 22 may be employed without departing from the scope of the present disclosure.

The audio system 24 is used to issue commands to the operator 14 when performing a guided assessment during the method for detecting impairment of the operator 14. The audio system 24 includes one or more speakers located within the vehicle 12 and may also include one or more microphones.

The operator monitoring system 26 is used to monitor the operator 14 during operation of the vehicle 12. The operator monitoring system 26 uses the camera 20, as well as additional sensors (not shown), to collect information regarding the operator 14. The operator monitoring system 26 may use the display 18, as well as the audio system 24, to provide feedback to the operator 14 based on the collected information. For example, the operator monitoring system 26 may track an attentiveness of the operator 14 using the camera 20 and provide an auditory alert from the audio system 24 if the operator monitoring system 26 determines that the operator 14 is not attentive or falling asleep. Operator monitoring system 26 may also verify through facial recognition that the operator 14 who is the subject of the operator vehicle impairment detector system 10 is the actual operator 14 of the vehicle 12.

The human machine interface (HMI) 28 is used by the operator 14 to provide commands to the vehicle 12. The HMI 28 may be a touch screen display on an infotainment system, or a knob or button, or may be used to activate a voice command system via the audio system 24. In addition, the HMI 28 may include sensors for reading hand gesture inputs.

The start control 30 is used to start and stop the vehicle 12. The start control 30 may be used to start and stop either an internal combustion engine, hybrid electric motor, or electric motor in the vehicle 12. In the present disclosure, the vehicle operator impairment detector system 10 overrides the start control 30 based on an assessment of the impairment of the operator 14, as will be described in greater detail below.

The vehicle operator impairment detector system 10 is used to detect and assess operator gaze nystagmus. Nystagmus is defined as repetitive, uncontrolled movement of the eyes. These movements often result in reduced vision and depth perception and can affect balance and coordination. Nystagmus is highly correlated with operator impairment, including blood alcohol content exceeding 0.08 BAC. These involuntary eye movements can occur from side to side (horizontal nystagmus), up and down (vertical nystagmus), or in a circular pattern (rotary nystagmus). In the example provided, the vehicle operator impairment detector system 10 assesses horizontal gaze nystagmus (HGN) by detecting eye movements left-to-right along a horizontal x-axis relative to the operator 14 over time. However, it should be appreciated that vertical gaze nystagmus or rotary gaze nystagmus may also be assessed without departing from the scope of the present disclosure. In addition, nystagmus may be pendular or jerking. The jerking nystagmus may be jerk with accelerating velocity slow phase, jerk with decelerating velocity slow phase, or jerk with a linear velocity slow phase.

Figure 2A:
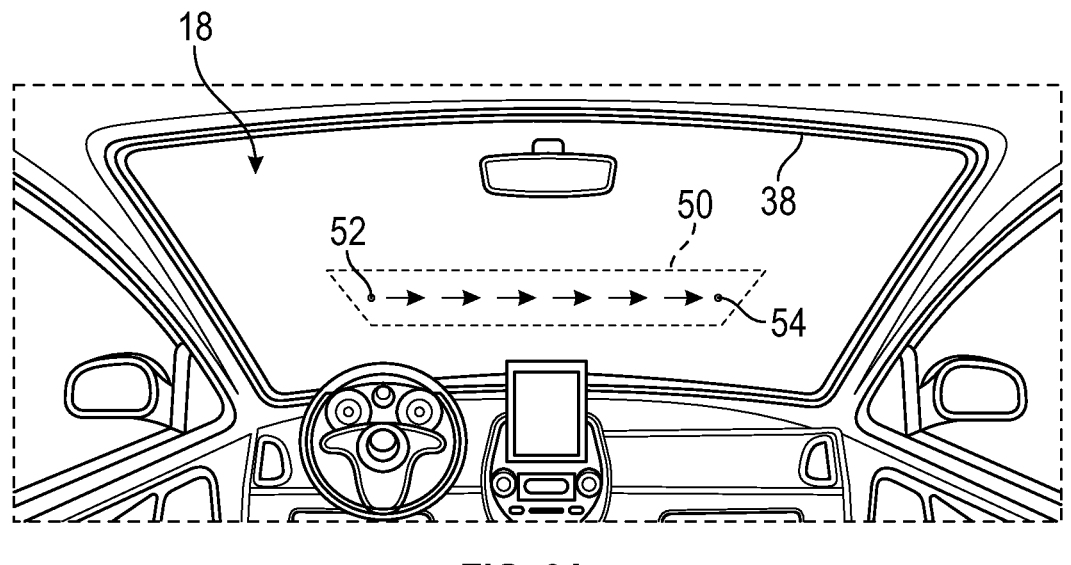
FIG. 2A is a schematic diagram of a display assessment used to assess gaze nystagmus using the vehicle operator impairment detector system.
Figure 2B:
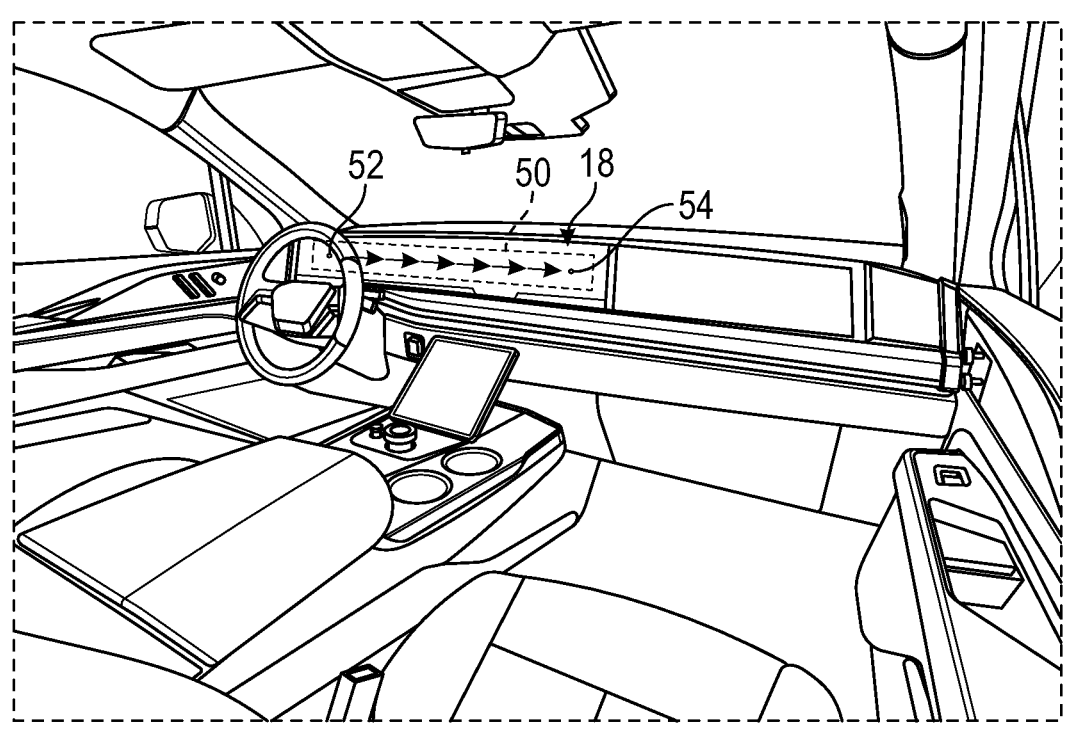
FIG. 2B is a schematic diagram of another example of a display assessment used to assess gaze nystagmus using the vehicle operator impairment detector system.
Figure 2C:
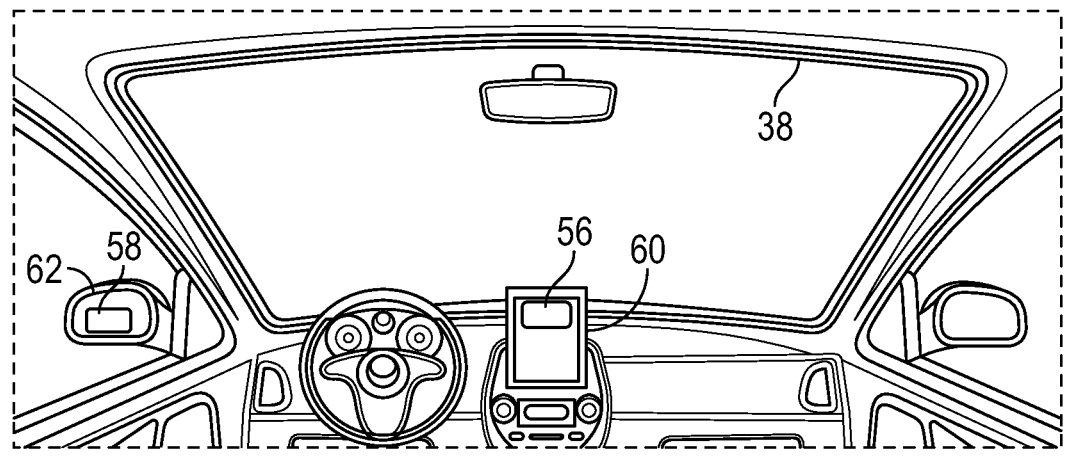
FIG. 2C is a schematic diagram of audio assessment used to assess gaze nystagmus using the vehicle operator impairment detector system.
Figure 2D:
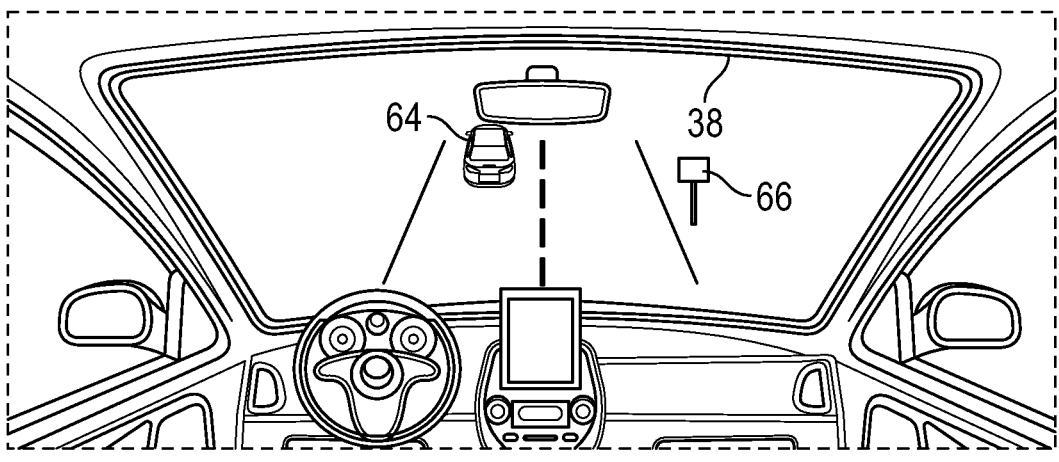
FIG. 2D is a schematic diagram of a passive assessment used to assess gaze nystagmus using the vehicle operator impairment detector system.

The vehicle operator impairment detector system 10 performs a gaze nystagmus assessment of the operator 14 to determine HGN using one of three methods: a display assessment shown in FIGS. 2A and 2B, an auditory assessment shown in FIG. 2C, and a passive assessment shown in FIG. 2D.

Referring to FIGS. 2A and 2B, the display assessment uses the display 18 to assess HGN of the operator. In FIG. 2A, the display 18 is a is a pillar-to-pillar HUD. Once the display assessment is initiated, the display 18 is used to project a graphic 50 on the windshield 38. In FIG. 2B, the display 18 is a wide-screen display on a console of the vehicle 12. Once the display assessment is initiated, the display 18 displays the graphic 50. The graphic 50 may be accompanied by voice command instructions provided by the audio system 24 or may include graphic or word instructions displayed on the display 18. The assessment includes instructing the operator 14 to fix on a first point 52 and move their eyes to a second point 54, each displayed on the display 18. The first point 52 is associated with a fixed location in front of the operator 14. The second point 54 is associated with a maximum eye position to the right of the operator 14. In one example, the graphic 50 allows the operator 14 to follow a visual prompt (e.g. moving dot) so the speed and angle of the gaze can be guided to meet diagnostic states that increase the probability of an accurate HGN assessment. In cases when a visual prompt can move continuously across the display 18 the operator 14 will be asked to follow a fixation point while keeping their head pose steady. The movement of the visual prompt will continue until sufficient eye position data is collected to make an assessment. Eye position is defined as the position of the eyes and head in space. Glance direction is defined as where the gaze is pointing. The camera 20 captures the x-axis direction of the eyes of the operator 14 over time as the eyes track the fixation point as it moves from the first point 52 to the second point 54. If the controller 16 determines that the operator 14 is not correctly following instructions during the assessment (for example, not keep their head steady or turned away from the camera 20), the controller 16 may issue corrective instructions. The captured data of the direction of the eyes over time is referred to as the gaze samples. In an alternate embodiment, the operator 14 may be instructed to keep their gaze fixed on a point and to rotate their head away from the point using visual or audio prompts.

Referring to FIG. 2B, the auditory assessment uses the audio system 24 to assess HGN of the operator. Once the assessment is initiated, the audio system 24 issues speech commands to the operator 14 to fix their gaze on a first location 56 in the vehicle 12 and then to shift their gaze to a second location 58 in the vehicle 12. In the example provided, the first location 56 is located on an infotainment system 6 60 and the second location 58 is located on a side view mirror 62. However, it should be appreciated that various other locations may be employed. The camera 20 captures the x-axis direction of the eyes of the operator 14 over time as the eyes move from the first location 56 to the second location 58. If the controller 16 determines that the operator 14 is not correctly following instructions during the assessment (for example, not keep their head steady or turned away from the camera 20), the controller 16 may issue corrective instructions. In an alternate embodiment, the operator 14 may be instructed to keep their gaze fixed on a location and to rotate their head using audio prompts.

Referring to FIG. 2C, the passive assessment tracks eye movement of the operator 14 during operation of the vehicle. Eye movement is tracked when the operator 14 has eye fixation on objects viewed through the windshield 38. For example, the camera 20 captures the x-axis direction of the eyes of the operator 14 as they move from a first object 64 in the roadway to a second object 66 adjacent the roadway. Head and gaze vectors monitored by the operator monitoring system 26 can assist in the assessment.

Once the gaze samples are collected using an HCN assessment as described above, the controller 16 passes the gaze samples through an HGN detection model to determine whether there is HGN. Generally, the HGN detection model includes two main parts: (1) a transformation of representation and (2) an estimate using a Gaussian Mixture Model (GMM).

The gaze samples are collected at a fixed interval during eye movements. The gaze sample that was collected at time $t_i$ may be denoted as: $(x, y, t)_i$ where are x, y are the horizontal and vertical direction of gaze respectively and t denotes the time. During the transformation of representation stage, the horizontal direction x is derived twice. The first derivative is the speed and denoted as dx:

$$dx = \frac{\partial x}{\partial t} = \frac{x_i - x_{i-1}}{t_i - t_{i-1}} \tag{1}$$

The second derivative is the horizontal acceleration of the gaze direction and denoted as ddx:

$$ddx = \frac{\partial dx}{\partial t} = \frac{dx_i - dx_{i-1}}{t_i - t_{i-1}} \tag{2}$$

However, estimations of the derivatives in Equations (1) and (2) may be noisy and a smoother estimation is needed or approximation is desired. The new representation $(dx, ddx, t)_i$ is invariance in terms of location and therefore the GMM is used to estimate the HGN from the gaze sample. For example, when analyzing data when the operator 14 has fixated their gaze on a single location, the $(x, y, t)_i$ data is concentrated at an arbitrary location while the $(dx, ddx, t)_i$ data is concentrated at about $(0,0)$ which by definition is a fixation of the gaze. Therefore, a Gaussian (normal distribution) with a mean at $(0,0)$ models the fixation gaze and its distribution has the following form:

$$P(dx, ddx) = \begin{array}{c} g(\mu, \Sigma) \\ \text{s.t.} \\ \mu = (0,0) \end{array} \tag{3}$$

Where g is normal distribution $N(\mu, \Sigma)$ and the parameters of a single Gaussian model are $\mu$, $\Sigma$ over $(dx, ddx)$ space. Overall, the parameters in Equation (3) are: $\mu$, $\Sigma$.

In another example, where the operator 14 has a fixated gaze on two different objects and a saccade (a rapid movement of the eye between fixation points) gaze therebetween, the $(x, y, t)_i$ representation would show the two fixations and a single behavior with a temporal pattern (e.g. saccade) between the two fixations. Meanwhile, the change of representation $(dx, ddx, t)_i$ joins the two fixations into one location $(0,0)$ and the temporal pattern is represented as a set of not concentrated points not at the location $(0,0)$. Therefore, this distribution is not a normal distribution and instead several Gaussians are assumed. The Gaussians are weighted, one Gaussian models the fixation (number 1 in Equation (4)) and a second Gaussian models the saccade (number 2 in Equation (4)):

$$P(dx, ddx) = \begin{array}{c} w_1 g_1(\mu_1, \Sigma_1) + w_2 g_2(\mu_2, \Sigma_2) \\ \text{s.t.} \\ \mu_1 = (0,0) \end{array} \tag{4}$$

Where $g_1$ and $g_2$ are two normal distributions $N(\mu, \Sigma)$ with parameters $\mu_1$, $\Sigma_1$ and $\mu_2$, $\Sigma_2$ respectively. In addition, each Gaussian has its own weight denoted by $w_1$ and $w_2$. Overall, the parameters in Equation (4) are: $w_1$, $\mu_1$, $\Sigma_1$, $w_2$, $\mu_2$, $\Sigma_2$.

In another example, the gaze samples are modeled using more than two Gaussians. In this general case, with a weighted mixture of Gaussians with G Gaussians, the distribution has the following form:

$$P(dx, ddx) = \sum_{i=1}^{G} w_i g_i(\mu_i, \Sigma_i) \qquad (5)$$

The parameters in Equation (5) are: $w_1$, $\mu_1$, $\Sigma_1$, . . . , $w_i$, $\mu_i$, $\Sigma_i$, . . . , $w_G$, $\mu_G$, $\Sigma_G$. Therefore, where the gaze samples are composed of several behavior patterns, the components of the GMM are allocated between the behavior patterns. This allocation is not predefined and occurs as part of the training of the GMM. The HGN model using the GMM determines whether there are micro eye movements, i.e. some amount of nystagmus, at the time intervals.

Figure 3:
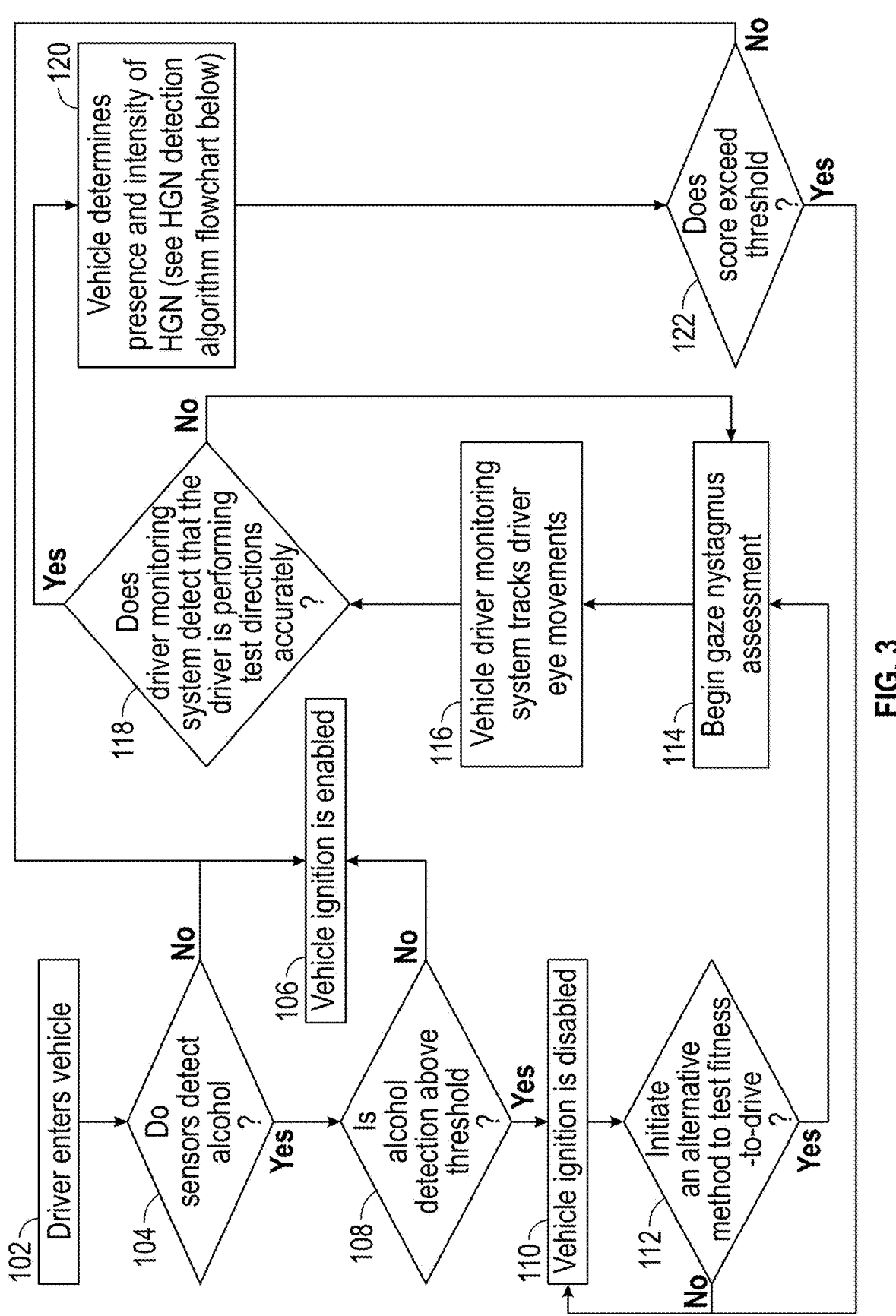
FIG. 3 is a flowchart of a method for determining operator impairment.

Turning to FIG. 3, the method 100 for detecting impairment of the operator 14 of the vehicle 12 is shown. The method 100 begins at step 102 when the operator 14 enters the vehicle 12. At this step, the vehicle 12 is off. The method 100 then proceeds to step 104.

At step 104 the controller 16 determines whether the alcohol sensor 22 detects alcohol. Depending on what type of alcohol sensor 22 is employed in the vehicle 12, the alcohol sensor 22 may detect alcohol (ethanol vapors) in the environment of the vehicle 12 and translate that alcohol concentration to an estimated blood alcohol concentration (BAC). Alternatively, where the infra-red scan of the operator's 14 finger is employed, the imaging from the operator 14 is analyzed by the controller 16 and the estimated BAC is determined. If no alcohol is detected, the method proceeds to step 106 and the start control 30 is enabled. When the start control 30 is enabled, the operator 14 is able to start the vehicle 12. If alcohol is detected, the method 100 proceeds to step 108.

At step 108, the controller 16 compares the estimated BAC to a BAC threshold. In one example, the BAC threshold is 0.08 BAC. However, the threshold may be set lower or higher based on local government rules. If the estimated BAC is lower than the BAC threshold, the method proceeds to step 106 and the start control 30 is enabled. However, if the estimated BAC is equal to or greater than the BAC threshold, the method proceeds to step 110 and the start control 30 is disabled. When the start control 30 is disabled, the operator 14 is prohibited from starting the vehicle 12. The method 100 then proceeds to step 112.

At step 112, the controller 16 determines whether the gaze nystagmus assessment has been initiated. The gaze nystagmus assessment is initiated by the operator 14 via the HMI 28. Alternatively, the gaze nystagmus assessment may be selected as a default setting or be conditioned on the estimated BAC (for example, an estimated BAC between 0.06 and 0.10 initiates the gaze nystagmus assessment). If the gaze nystagmus assessment has not been initiated, then method 100 returns to step 110 and the start control 30 remains disabled for a fixed amount of time or until the controller 16 detects entry of another operator 14 of the vehicle 12. If the gaze nystagmus assessment has been initiated, the method 100 proceeds to step 114.

At step 114, the gaze nystagmus assessment is performed. The gaze nystagmus assessment uses one of the display assessment shown in FIG. 2A, the auditory assessment shown in FIG. 2B, or the passive assessment shown in FIG. 2C. The method 100 then proceeds to step 116.

At step 116, the operator monitoring system 26 tracks the eye positions of the operator 14 at time intervals using the camera 20 during the gaze nystagmus assessment. As noted above, the tracked eye directions are comprised of gaze samples that include the x-axis direction of the eyes of the operator 14 at time intervals. The method 100 then proceeds to step 118.

At step 118, the controller 16 uses the operator monitoring system 26 to determine if the operator 14 is performing the gaze nystagmus assessment correctly. The gaze nystagmus assessment is performed incorrectly when some factor interferes with the accurate collection of the gaze samples. For example, if the operator 14 moves their head during the assessment, or closes their eyes during the assessment, or the eyes are not visible due to glasses or sunglasses, the gaze samples may be unreliable and the assessment is not being performed correctly. If the assessment is not performed correctly, the method returns to step 114 and the gaze nystagmus assessment is restarted. Optionally, the controller 16 may issue corrective instructions via the display 18 and/or the audio system 24. If the assessment is performed correctly, the method 100 proceeds to subroutine 120.

At subroutine 120, the controller 16 determines whether gaze nystagmus is present based on the gaze samples collected during the gaze nystagmus assessment and determines an intensity of the gaze nystagmus when present. As will be described in greater detail below, the presence and intensity of gaze nystagmus for each eye of the operator 14 is determined using the gaze nystagmus model. As noted previously, the gaze nystagmus model transforms the gaze samples using two derivatives and estimates a GMM using the derivatives to determine whether there are micro eye movements (i.e., some form of nystagmus). Amplitude and frequency (i.e., intensity) of the micro eye movements is determined from the gaze samples. In one embodiment, the controller 16 assigns a numerical score based on the presence and intensity of nystagmus for each eye. The method 100 then proceeds to step 122.

At step 122, the controller 16 determines whether the presence and intensity of nystagmus determined in subroutine 120 indicates the operator 14 is impaired. For example, where a numerical score is assigned at subroutine 120, the controller 16 compares the score to an impairment threshold. The impairment threshold is four in the example provided but may be adjusted lower or higher based on local laws. If the score is greater than or equal to the impairment threshold, the operator 14 is impaired and the method returns to step 110 and the start control 30 is disabled. If the score is less than the impairment threshold, the operator 14 is not impaired, and the method 100 proceeds to step 106 and the start control 30 is enabled, despite the detection of alcohol at step 108.

Figure 4:
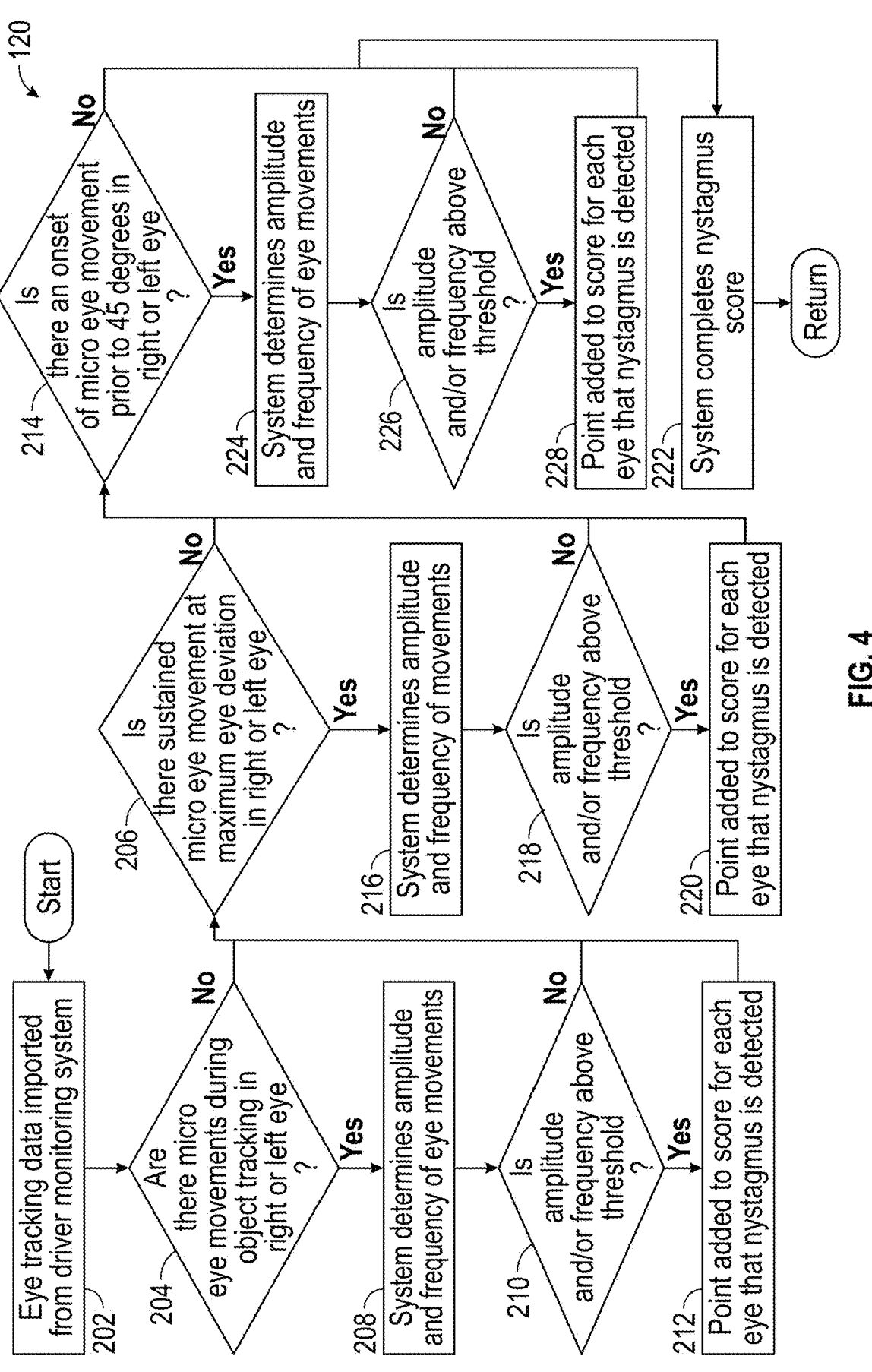
FIG. 4 is a flowchart of a subroutine for determining presence and intensity of gaze nystagmus.

Turning to FIG. 4, the subroutine 120 to determine whether gaze nystagmus is present based on the gaze samples collected during the gaze nystagmus assessment and determine an intensity of the gaze nystagmus when present will be described in greater detail. The subroutine 120 starts at step 202 where the eye tracking data, including the gaze samples, are imported from the operator monitoring system 26 to the controller 16. The subroutine 120 then proceeds to step 204.

At step 204, the controller 16 determines whether there are micro eye movements in the right or left eye during the time intervals associated with the full eye movement during the gaze nystagmus assessment. For example, the time intervals used at this step are associated with full movement of the eyes from the first point 52 to the second point 54 or the first location 56 to the second location 58 during the gaze assessment. The controller 16 determines the presence of micro eye movements based on the gaze nystagmus model. If no micro eye movements are detected for either eye, the subroutine 120 proceeds to step 206. If micro eye movements are detected for either eye, the subroutine 120 proceeds to step 208.

Figure 5:
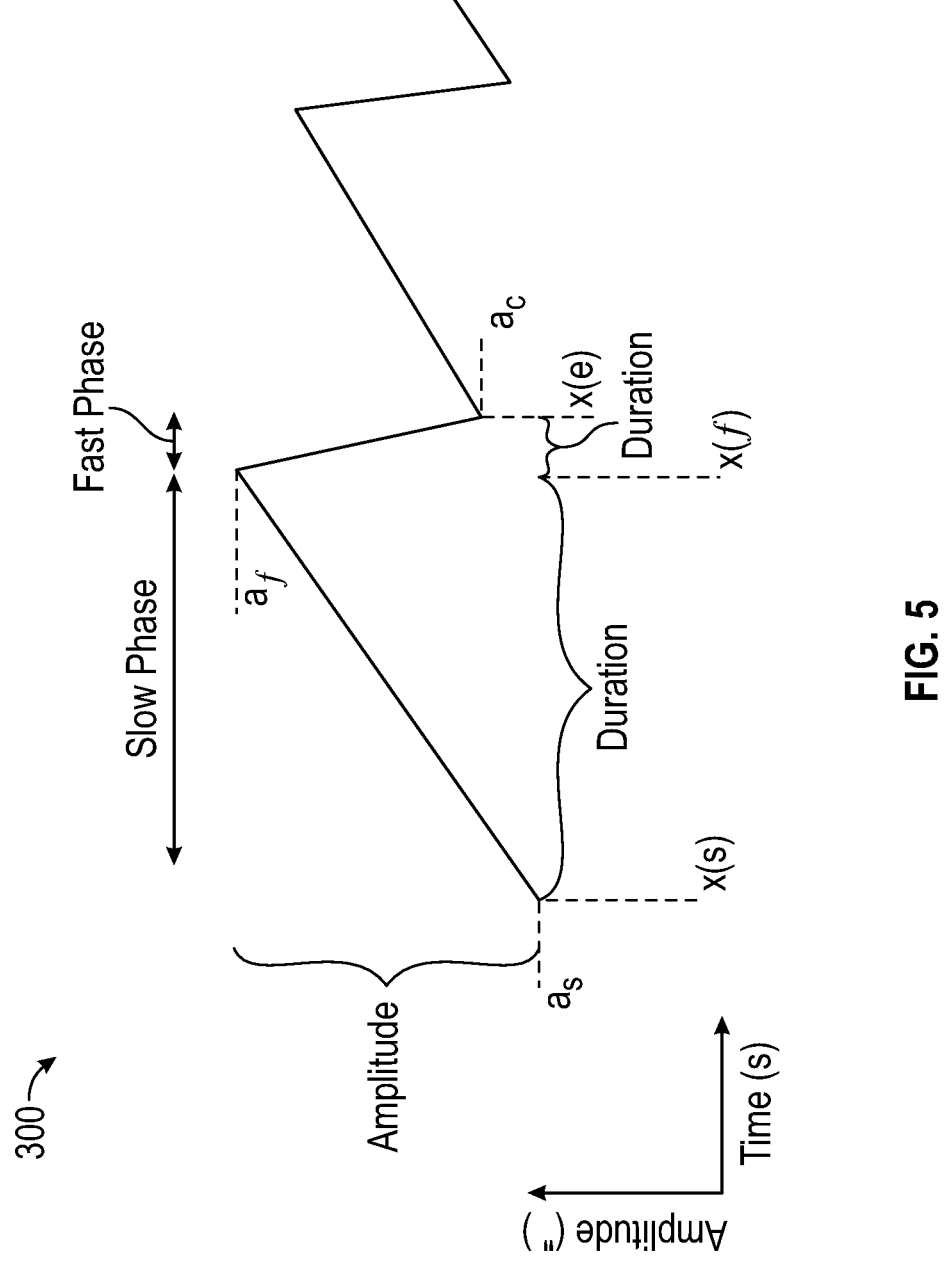
FIG. 5 is a graph illustrating gaze nystagmus.

At step 208, the controller 16 determines an amplitude and a frequency of the detected micro eye movements for each eye using the gaze samples. The amplitude is defined as the difference between x-axis positions of the eye during a slow phase of a detected micro eye movement. The frequency is defined as the number of detected micro eye movements over a time interval. An example of a graph showing HGN jerk with linear velocity slow phase is shown in FIG. 5 and indicated by reference number 300. The graph 300 illustrates an amplitude of a micro eye movement between times(s) and (f) during the slow phase. The amplitude may be an average of amplitudes of the slow phases over the eye movement. Returning to FIG. 4, the subroutine 120 then proceeds to step 210.

At step 210, the controller 16 compares the amplitude and frequency detected during the full eye movement to a first amplitude threshold and a first frequency threshold, respectively. The first amplitude threshold and first frequency threshold may be set by local laws or government guidelines. If the amplitude or the frequency during the full eye movement is less than the first amplitude threshold and the first frequency threshold, the subroutine 120 proceeds to step 206. If the amplitude and the frequency during the full eye movement is equal to or greater than the first amplitude threshold and the first frequency threshold, the subroutine 120 proceeds to step 212.

At step 212, the controller 16 assigns a score for each eye in which nystagmus is detected and has an intensity greater than the thresholds. The subroutine 120 then proceeds to step 206.

At step 206, the controller 16 determines whether there are micro eye movements in the right or left eye during the time intervals associated with the maximum eye movement during the gaze nystagmus assessment. For example, the time intervals used at this step are associated with the eyes fixated on the first point 52 or the first location 56 during the gaze assessment. The controller 16 determines the presence of micro eye movements based on the gaze nystagmus model. If no micro eye movements are detected for either eye, the subroutine 120 proceeds to step 214. If micro eye movements are detected for either eye, the subroutine 120 proceeds to step 216.

At step 216, the controller 16 determines an amplitude and a frequency of the detected micro eye movements for each eye using the gaze samples at the maximum eye position. The amplitude is defined as the difference between x-axis positions of the eye during a slow phase of a detected micro eye movement. The frequency is defined as the number of detected micro eye movements over a time interval. The amplitude may be an average of amplitudes of the slow phases over the eye movement. The subroutine 120 then proceeds to step 218.

At step 218, the controller 16 compares the amplitude and frequency at the maximum horizontal eye position to a second amplitude threshold and a second frequency threshold, respectively. The second amplitude threshold and second frequency threshold may be set by local laws or government guidelines. If the amplitude or the frequency at the maximum eye position is less than the second amplitude threshold and the second frequency threshold, the subroutine

120 proceeds to step 214. If the amplitude and the frequency at the maximum eye position is equal to or greater than the second amplitude threshold and the second frequency threshold, the subroutine 120 proceeds to step 220.

At step 220, the controller 16 assigns a score for each eye in which nystagmus is detected and has an intensity greater than the thresholds. The subroutine 120 then proceeds to step 214.

At step 214, the controller 16 determines whether there are micro eye movements in the right or left eye prior to the eyes passing forty-five degrees from the start or center position during the gaze nystagmus assessment. The forty-five degrees from starting eye position is equivalent to a midpoint position between an eye start position and the maximum eye position during the gaze nystagmus assessment. For example, the time intervals used at this step are associated with movement of the eyes between the first point 52 and a midpoint between the first point 52 and the second point 54 or movement of the eyes between the first location 56 and a midpoint between the first location 56 and the second location 58 during the gaze assessment. The controller 16 determines the presence of micro eye movements based on the gaze nystagmus model. If no micro eye movements are detected for either eye, the subroutine 120 proceeds to step 222. If micro eye movements are detected for either eye, the subroutine 120 proceeds to step 224.

At step 224, the controller 16 determines an amplitude and a frequency of the detected micro eye movements for each eye from the gaze samples prior to 45 degrees. The amplitude is defined as the difference between x-axis positions of the eye during a slow phase of a detected micro eye movement. The frequency is defined as the number of detected micro eye movements over a time interval. The amplitude may be an average of amplitudes of the slow phases over the eye movement. The subroutine 120 then proceeds to step 226.

At step 226, the controller 16 compares the amplitude and frequency prior to the 45 degree eye position to a third amplitude threshold and a third frequency threshold, respectively. The third amplitude threshold and third frequency threshold may be set by local laws or government guidelines. If the amplitude or the frequency prior to the 45 degree eye position is less than the third amplitude threshold and the third frequency threshold, the subroutine 120 proceeds to step 222. If the amplitude and the frequency prior to the 45 degree eye position is equal to or greater than the third amplitude threshold and the third frequency threshold, the subroutine 120 proceeds to step 228.

At step 228, the controller 16 assigns a score for each eye in which nystagmus is detected and has an intensity greater than the thresholds. The subroutine 120 then proceeds to step 222.

At step 222, the controller 16 compiles (i.e., adds) the individual scores for each eye for each test to determine the overall score. Subroutine 120 then ends and proceeds to step 122 in FIG. 3.

It should be appreciated that steps 204, 206, and 214 may be taken in a different order without departing from the scope of the present disclosure. Moreover, the first, second, and third amplitude thresholds may be the same and the first, second, and third frequency thresholds may be the same without departing from the scope of the present disclosure.

The system 10 and method 100 of the present disclosure offer several advantages. First, the system 10 and method 100 allow for an override of false positives due to the alcohol sensor 22 malfunctioning or detecting airborne chemicals. Second, the system 10 and method 100 can determine actual impairment due to nystagmus, even if no alcohol is detected. Finally, the system 10 and method 100 provide repeatability, consistency, and increased accuracy when determining nystagmus.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A system for detecting an impairment of an operator of a vehicle, the system comprising:

an alcohol sensor;

a camera;

a start control; and a controller in electrical communication with the alcohol sensor, the camera, and the start control, the controller including a processor and a memory, the memory including instructions such that the processor is programmed to:

determine that alcohol is detected using the alcohol sensor;

disable the start control based on the detection of alcohol;

perform a gaze nystagmus assessment of the operator using the camera and using a display assessment using a display in the vehicle by tracking an eye movement of the operator and recording gaze samples over time during the eye movement, wherein the gaze samples include horizontal positions of the eyes during the eye movement of the operator at time intervals;

transform the gaze samples by deriving the horizontal positions of the eyes twice to determine a velocity and an acceleration at each time interval;

estimate a Gaussian Mixture Model using the derivatives of the horizontal positions of the eyes to determine if there are micro eye movements during the time intervals and to determine an amplitude and frequency of the micro eye movements at the time intervals;

determine if the operator is impaired based on the gaze nystagmus assessment by determining if there are micro eye movements during the time intervals during the eye movement, determine if there are micro eye movements during the time intervals at a maximum horizontal eye position, and determine if there are micro eye movements during the time intervals prior to forty-five degrees from a center during eye movement; and enable the start control when the operator is not impaired.

2. The system of claim 1, wherein the processor is further programmed to:

determine if the operator is impaired by comparing the amplitude and the frequency of the micro eye movements during the eye movement to a first amplitude threshold and a first frequency threshold, and determine nystagmus is detected when the amplitude and the frequency during the eye movement is greater than the first amplitude threshold and the first frequency threshold.

3. The system of claim 2, wherein the processor is further programmed to:

determine if the operator is impaired by comparing the amplitude and the frequency of the micro eye movements during the time intervals at the maximum horizontal eye position to a second amplitude threshold and a second frequency threshold, and determine nystagmus is detected when the amplitude and the frequency during the time intervals at the maximum horizontal eye position is greater than the second amplitude threshold and the second frequency threshold.

4. The system of claim 3, wherein the processor is further programmed to:

determine if the operator is impaired by comparing the amplitude and the frequency of the micro eye movements during the time intervals prior to forty-five degrees from the center during eye movement to a third amplitude threshold and a third frequency threshold, and determine nystagmus is detected when the amplitude and the frequency during the time intervals prior to forty-five degrees from the center during eye movement is greater than the third amplitude threshold and the third frequency threshold.

5. The system of claim 4, wherein the processor is further programmed to:

assign a score for each eye based on whether nystagmus was detected during the time intervals and comparing the score to an impairment threshold; and determine the operator is impaired when the score exceeds the impairment threshold.

6. A method for detecting an impairment of an operator of a vehicle, the method comprising:

providing an alcohol sensor, a camera, a start control, and a controller in electrical communication with the alcohol sensor, the camera, and the start control, the controller including a processor and a memory;

determining that alcohol is detected using the alcohol sensor disposed within the vehicle;

disabling the start control based on the detection of alcohol within the vehicle;

performing a gaze nystagmus assessment of the operator using the camera within the vehicle and using a display assessment using a display in the vehicle by tracking an eye movement of the operator and recording gaze samples over time during the eye movement, wherein the gaze samples include horizontal positions of the eyes during the eye movement of the operator at time intervals;

transforming the gaze samples by deriving the horizontal positions of the eyes twice to determine a velocity and an acceleration at each time interval;

estimating a Gaussian Mixture Model using the derivatives of the horizontal positions of the eyes to determine if there are micro eye movements during the time intervals and to determine an amplitude and frequency of the micro eye movements at the time intervals;

determining that the operator is not impaired based on the gaze nystagmus by determining if there are micro eye movements during the time intervals during the eye movement, determine if there are micro eye movements during the time intervals at a maximum horizontal eye position, and determine if there are micro eye movements during the time intervals prior to forty-five degrees from a center during eye movement; and enabling the start control when the operator is not impaired.

7. The method of claim 6, wherein determining if the operator is impaired includes comparing the amplitude and the frequency of the micro eye movements during the eye movement to a first amplitude threshold and a first frequency threshold, and determining nystagmus is detected when the amplitude and the frequency during the eye movement is greater than the first amplitude threshold and the first frequency threshold.

8. The method of claim 7, wherein determining if the operator is impaired includes comparing the amplitude and the frequency of the micro eye movements during the time intervals at the maximum horizontal eye position to a second amplitude threshold and a second frequency threshold, and determining nystagmus is detected when the amplitude and the frequency during the time intervals at the maximum horizontal eye position is greater than the second amplitude threshold and the second frequency threshold.

9. The method of claim 8, wherein determining if the operator is impaired includes comparing the amplitude and the frequency of the micro eye movements during the time intervals prior to forty-five degrees from the center during eye movement to a third amplitude threshold and a third frequency threshold, and determining nystagmus is detected when the amplitude and the frequency during the time intervals prior to forty-five degrees from the center during eye movement is greater than the third amplitude threshold and the third frequency threshold.

10. The method of claim 9, further comprising:
assigning a score for each eye based on whether nystagmus was detected during the time intervals and comparing the score to an impairment threshold; and
determining the operator is impaired when the score exceeds the impairment threshold.

11. A system for detecting an impairment of an operator of a vehicle, the system comprising:
an alcohol sensor;
a camera;
a display on the vehicle;
a start control; and
a controller in electrical communication with the alcohol sensor, the camera, the display, and the start control, the controller including a processor and a memory, the memory including instructions such that the processor is programmed to:
determine that alcohol is detected using the alcohol sensor;
disable the start control based on the detection of alcohol;
perform a gaze nystagmus assessment of the operator including displaying a graphic on the display, instructing the operator to follow the graphic on the display with their eyes, and tracking an eye movement using the camera to record gaze samples over time intervals;
transform the gaze samples by deriving horizontal positions of the eyes twice to determine a velocity and an acceleration at each time interval;
estimate a Gaussian Mixture Model using the derivatives of the horizontal positions of the eyes to determine if there are micro eye movements during the time intervals;
determine an amplitude and frequency of the micro eye movements at the time intervals when there are micro eye movements;
compare the amplitude and frequency of the micro eye movements throughout a full eye movement, at a maximum eye position, and prior to a midpoint of the full eye movement to one or more thresholds;
assign a score for each eye when the amplitude and frequency of the micro eye movements at the full eye movement, at the maximum eye position, and prior to the midpoint of the full eye movement exceeds the one or more thresholds;
compare the score to an impairment score; and
enable the start control when the score is less than the impairment score and disable the start control when the score is greater than or equal to the impairment score.

* * * * *